United States Patent
Yakimuk et al.

(10) Patent No.: US 8,030,493 B2
(45) Date of Patent: Oct. 4, 2011

(54) MONOVALENT AND DIVALENT SALTS OF N-(5-HYDROXYNICOTINOIL)-L-GLUTAMIC ACID EXHIBITING PSYCHOTROPIC (ANTIDEPRESSANT AND ANXIOLYTIC), NEUROPROTECTIVE, GEROPROTECTIVE AND CEREBROPROTECTIVE ACTION

(75) Inventors: Pavel Vasilyevich Yakimuk, Moscow (RU); Sergey Vitalyevich Stovbun, Moskovskaya obl. (RU); Alexandr Anatolyevich Litvin, Moscow (RU)

(73) Assignee: Obschestvo S Ogranichennoy Otvetstvennostyu "Natsionalnaya Isseldovatelskaya Kompaniya", Tulskaya obl. (RU)

( * ) Notice: Subject to any disclaimer, the term of this patent is extended or adjusted under 35 U.S.C. 154(b) by 310 days.

(21) Appl. No.: 12/309,543

(22) PCT Filed: Jun. 6, 2007

(86) PCT No.: PCT/RU2007/000304
§ 371 (c)(1),
(2), (4) Date: Jan. 22, 2009

(87) PCT Pub. No.: WO2008/018815
PCT Pub. Date: Feb. 14, 2008

(65) Prior Publication Data
US 2009/0240059 A1    Sep. 24, 2009

(30) Foreign Application Priority Data

Jul. 31, 2006 (RU) .................. 2006127564

(51) Int. Cl.
*C07D 213/04*  (2006.01)
(52) U.S. Cl. ........................................ 546/298
(58) Field of Classification Search ............... None
See application file for complete search history.

(56) References Cited

FOREIGN PATENT DOCUMENTS

| RU | 94038232 | 8/1996 |
|----|----------|--------|
| SU | 1368314  | 1/1988 |

OTHER PUBLICATIONS

International Search Report, Oct. 18, 2007.
Voronina T.A. et al. "Novoe veschestvo s novotropnoi aktivnostiju-N-(5-oxinikotinoli)-L-glutaminovaya kislota." ("New compound with nootropic activity N-(5-oxynicotinoyl)-L-glutamic acid Pharmacologia I Toxicologia") Farmakologiya I toxikologiya, 1990, vol. 53, No. 4, pp. 13-16. (ISR) (Spec., p. 2).

*Primary Examiner* — Zinna Northington Davis
(74) *Attorney, Agent, or Firm* — Collard & Roe, P.C.

(57) ABSTRACT

The invention relates to medicine, in particular to mono- and divalent salts of N-(5-hydroxynicotinoil)-L-glutaminic acid exhibiting psychotropic antidepressant, anxiolytic, heroprotective, neuroprotective, antihypoxia cerebroprotective and nootropic action. The novel compounds differ from the known preparations, including the closest prior art in the form of a N-(5-hydroxynicotinoil)-L-glutaminic acid base (nooglucotyl), in that they produce psychotropic effects, namely antidepressant, anxiolytic, neuroprotective and heroprotective actions, in such a way that lesion focuses caused by apoplectic attacks are reduced and age-specific neurological deficiencies and intellectual and physical work capacities are improved.

1 Claim, No Drawings

MONOVALENT AND DIVALENT SALTS OF N-(5-HYDROXYNICOTINOIL)-L-GLUTAMIC ACID EXHIBITING PSYCHOTROPIC (ANTIDEPRESSANT AND ANXIOLYTIC), NEUROPROTECTIVE, GEROPROTECTIVE AND CEREBROPROTECTIVE ACTION

CROSS REFERENCE TO RELATED APPLICATIONS

This application is the National Stage of PCT/RU2007/000304 filed on Jun. 6, 2007, which claims priority under 35 U.S.C. §119 of Russian Application No. 2006127564 filed on Jul. 31, 2006. The international application under PCT article 21(2) was not published in English.

FIELD OF INVENTION

The invention relates to medicine, namely, to new biologically active compounds, more specifically—to mono- and divalent salts of N-(5-hydroxynicotinoyl)-L-glutamic acid, which produce psychotropic (antidepressant, anxiolytic), geroprotective, neuroprotective, cerebroprotective action, which can be used for therapy of depressions, ischemic and hemorrhagic strokes, age-dependent deficiencies and other diseases associated with anxiety, depression, cognitive impairment and neurodegeneration.

STATE OF THE ART

At present depression and anxiety are the most common mental diseases, which are often associated with other conditions, including ageing, strokes, cancer, Alzheimer's disease, and Parkinson's disease etc.

Stroke (vascular cerebral affection) takes the second and the third places as the cause of mortality in Russia and in the world, respectively. The incidence of ischemic strokes (failure of blood supply of the brain) comprises 70-80%, and the incidence of hemorrhagic strokes (cerebral hemorrhage) is 20-30%. These two forms of the stroke differ in pathogenesis and require different therapeutic approaches; however neurodegenerative processes are observed with all forms of the stroke. Differential diagnosis of these two forms of the stroke is difficult at early stages of the disease, and in more than 25% cases it is just unfeasible. In this connection, it is advisable to create the agents, which are efficacious in patients with both forms of the stroke. At present calcium channel antagonists are used for the stroke, however, these agents have important side effects and disadvantages, such as cardiovascular effects leading to steal phenomenon of the brain.

Cognitive impairment and hypoxic conditions are observed with many diseases both in children and in the course of natural ageing process, stresses and diseases associated with neurodegeration. Antihypoxic and nootropic agents can be used in therapy of the patients with impairment of mental function developed due to ageing, Alzheimer's disease, after cerebral trauma, prenatal hypoxia, in alcohol abusers, in patients with vegetative neurosis and other diseases. Pyracetam, which is used for these conditions, is a low potent agent.

Chemical structure of nooglutyl (N-(5-hydroxynicotinoyl)-L-glutamic acid) is most similar to new suggested compounds. However, nooglutyl does not exhibit psychotropic (antidepressant and anxyolytic) and neuroprotective effects (SU patent No 1368314 published in BI No 3, 1988, and "N-nicotinoyl amino acids of antihypoxic and antiamnestic activity"; Voronina T. A. et al. "New compound with nootropic activity N-(5-oxynicotinoyl)-L-glutamic acid "Pharmacologia I Toxicologia", 1990, v. 53, No 4, p. 13-16).

ESSENCE OF THE INVENTION

This invention was aimed on creation of novel highly efficacious and low toxic compounds combining psychotropic (anxiolytic, antidepressant) effects with neuroprotective, cerebroprotective, geroprotective, antihypoxic effects, improving learning capacity and thus having the advantages over the known agents.

This objective was achieved through creation of new compounds, specifically, monovalent and divalent salts of N-(5-hydroxynicotinoyl)-L-glutamic acid (compounds I, II, and III) of general formula:

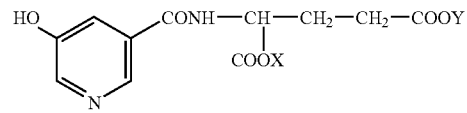

wherein
x=CaOH, y=H (I), or
x=y=Na (II), or
x=y=K (III),
which exhibit antidepressant, anxiolytic, neuroprotective cerebroprotective, geroprotective, nootropic, antihypoxic activities.

Claimed compounds fundamentally differ from nooglutyl by the presence of psychotropic (antidepressant and anxiolytic) and neuroprotective pharmacological effects, and by higher psychotropic potency.

Claimed compounds are white crystalline compounds, insoluble in methyl, ethyl, and isopropyl alcohols, almost insoluble in benzene, trichloromethane, ethyl acetate, and other organic solvents. These compounds are soluble in water, diluted acid and alkali solution.

Compounds, which are claimed in this patent, are new and not described in literature.

EMBODIMENTS OF THE INVENTION

EXAMPLE 1

Heat suspension of 2.68 g (0.01M) of N-(5-hydroxynicotinoyl)-L-glutamic acid in 50 ml of water up to 60-70° C. and add 0.68 g (0.012M) of calcium oxide in small portions. The sediment gradually dissolves. Heat the suspension for complete dissolution. Evaporate aquatic solution to 20 ml. Add resultant solution dropwise to 200 ml of ethanol. Mix formed precipitate for 0.5 hour and leave it for 12 hours at room temperature. Filter the precipitate, wash with alcohol and dry at 100° C. for constant weight (3 hours). Calcium N-(5-hydroxynicotinoyl)-L-glutamate (I) is obtained, recovery is 2.7 g (83%), $[\alpha]_D^{20}+11°$ (c 1, water).

Found, %: C 40.80; H 3.64; N 8.80. $C_{11}H_{12}CaN_2O_7$ or $C_{11}H_{10}CaN_2O_6 \cdot 1H_2O$ for chelate. Rectify using proton magnetic resonance).

Calculated, %: C 40.76; H 3.70; N 8.64.

IR-spectrum (in KBr), cm$^{-1}$.

UV-spectrum (in water): λ max.

PMR spectrum (in $D_2O$), internal standard: hexamethyldisiloxane.

EXAMPLE 2

Heat suspension of 0.27 g (0.001M) of N-(5-hydroxynicotinoyl)-L-glutamic acid in 5 ml of water up to 50-60° C. and carefully add 0.2 g (0.0024M) of sodium bicarbonate in small portions. Heat the suspension to achieve complete dissolution, and evaporate in vacuum to dryness. Add ethanol to the residue and evaporate in vacuum again. Grind the residue with dry ether and filter precipitate. Then dry precipitate at 60° C./1 mmHg, and obtain di-Na salt of N-(5-hydroxynicotinoyl)-L-glutamic acid (II), recovery 0.25 g (80.6%).

$[\alpha]_D^{20}$+13.7° (c 1, water).
Found, %: C 42.51; H 3.46; N 9.15. $C_{11}H_{10}Na_2N_2O_6$.
Calculated, %: C 42.31; H 3.23; N 8.97.
IR-spectrum (in KBr), $cm^{-1}$.
UV-spectrum (in water): $\lambda$ max.
PMR spectrum (in $D_2O$), internal standard: HMDS.

EXAMPLE 3

Heat suspension of 0.27 g (0.001M) of N-(5-hydroxynicotinoyl)-L-glutamic acid in 5 ml of water up to 50-60° C. and carefully add 0.24 g (0.0024M) of potassium bicarbonate in small portions. Heat the suspension to achieve complete dissolution, and evaporate in vacuum to dryness. Add ethanol to the residue and evaporate in vacuum again. Grind the residue with dry ether and filter precipitate, wash with dry ether and dry precipitate at 60° C./1 mmHg, and obtain di-K salt of N-(5-hydroxynicotinoyl)-L-glutamic acid (III), recovery 0.27 g (79.4%).

$[\alpha]_D^{20}$+10.5° (c 1, water).
Found, %: C 38.64; H 3.15; N 8.35. $C_{11}H_{10}K_2N_2O_6$.
Calculated, %: C 38.36; H 2.93; N 8.14.
IR-spectrum (in KBr), $cm^{-1}$.
UV-spectrum (in water): $\lambda$ max.
PMR spectrum (in $D_2O$), internal standard: HMDS.

Further the examples illustrating efficacy of the salts of N-nicotinoyl glutamic acids are given, which exhibit cerebroprotective, antihypoxic, antidepressive, anxiolytic effects, and improve both memory and learning ability.

EXAMPLE 4

Study of Antihypoxic Activity of the Salts of N-Nicotinoyl Glutamic Acids

Antihypoxic effect was studied under conditions of two procedures: hypobaric hypoxia and hypoxia with hypercapnia in hermovolume (Voronina T. A. et al. "Textbook for Experimental (Preclinical Study) of novel pharmacological compounds". Moscow, Medicina. 2005, p. 308-320). White nondescript male mice with body weight 22-28 g were used in the experiments. Each dose level was studied in 10 animals. Control animals received equivalent volume of distilled water. Nooglutyl was used as reference agent. Study compounds were administered intraperitoneally 40 minutes before the experiment.

Acute hypobaric hypoxia was simulated in flow-exhaust chamber. Pressure was measured with altimeter, and elevation speed with variometer. The animals were "elevated" at the speed 20 m/s to the stage at 11000 m. The exposure lasted 10 minutes. Then the animals were mover down to the baseline level for 5 minutes. Hypoxia with hypercapnia in hermovolume was created by placement of the animal into 200 ml hermetically sealed glass vessels. Life period of the animals under hypoxic conditions was recorded. Each group comprised 10 animals.

The experiments showed that after exposure to hypobaric hypoxia for 10 minutes all control animals died; average life period was 3.6 minutes. All studied compounds I-III were able to increase the life period of mice under conditions of acute oxygen deficiency in pressure chamber, and Compound I was the most potent. Compound I exhibited effect at lower doses compared with nooglutyl. When similar doses 30 and 60 mg/kg were used Compound I produced more pronounced effect compared with nooglutyl (Table 1).

Under conditions of hypoxia with hypercapnia in hermovolume average life period of control animals was 14.3 minutes. All studied compounds I-III were able to prolong the life period of the mice under conditions of hypoxia with hypercapnia in hermovolume, and Compound I was the most potent. Effect of Compound I was realized at the lower doses than with nooglutyl. When similar doses 30 and 60 mg/kg were used Compound I produced more pronounced effect compared with nooglutyl (Table 1).

EXAMPLE 5

Study of Antiamnestic Activity of the Salts of N-Nicotinoyl Glutamic Acids

White nondescript male rats with body weight 250-280 g were used in the experiments. Each dose level was studied in 10 animals. Control animals received equivalent volume of distilled water. Nooglutyl was used as reference agent. Study compounds were administered intraperitoneally 40 minutes before the experiment. Experiment was carried out on the standard automated unit for passive avoidance response (Passive Avoidance) supplied by Lafayette Instrument Co., (USA) (Ader et al. Retention of a passive avoidance response as a function of the intensity and duration of electric shock. Psycho Sci. 1972, v. 26, p. 125-128; Voronina T. A. et al. "Textbook for Experimental (Preclinical Study) of novel pharmacological compounds". Moscow, Medicina. 2005, p. 253-263 and 308-320). The unit was designed as small platform situated 1 m above the floor, which was illuminated with special lamp, and dark chamber with electrode floor connected with the platform. The rat was placed on illuminated platform in front of the entry to the dark chamber with its tail directed to the entry; the animal preferred dark chamber and quickly ran into it. In the dark chamber the animal received single pain stimulus with electric current (0.45 mA) and memorized that it was dangerous to enter dark chamber. Duration of the stimulus was determined from the running out of the animal from the dark chamber. To achieve amnesia maximum electric shock was used (50 Hz, 0.2 sec), which was made through corneal electrodes immediately after learning. Electric shock caused obliteration of the memory trace. Test for reproduction of passive avoidance response (PAR) (for retention of memory trace) was performed 24 hours after learning session and electric shock. The animal was placed on illuminated platform once again, and time of the presence on illuminated platform and dangerous dark chamber (no current was conducted to the floor during reproduction of PAR).

Control trained animals with reproduction of PAR without electric shock preferred to stay on illuminated platform. Obliteration of training with electric shock causes amnesia in the animals; as a result, the animals with short latent period enter dark chamber and stay there considerably longer than animals without amnesia (Table 2).

All studied compounds exhibited marked antiamnestic activity, which was manifested by that the time of the presence of the animals on safe illuminated platform is significantly greater compared with control animals with amnesia. The highest antiamnestic potency was found in Compound I, which was superior to nooglutyl (Table 2). Statistically significant effect of nooglutyl was found at the dose level 50 mg/kg, while effect of the same intensity was achieved by Compound I at dose level 25 mg/kg, indicating higher potency of Compound I compared with nooglutyl.

EXAMPLE 6

Study of the Efficacy of Salt of N-Nicotinoyl Glutamic Acid (Compound I) and Nooglutyl in the Model of Massive Cortical Ischemia White nondescript male rats with body weight 350-450 g anesthetized with chloral hydrate (400 mg/kg, intraperitoneally) were used in the experiments. After ligation of left carotid occlusion of middle cerebral artery (OMCA) was made under the microscope (magnification 14.0×3.3) proximal to bifurcation to frontal and parietal branches (S. T. Chen et al., Stroke, 1986, v. 17, No 4, p. 738-743).

After the surgery the animals were randomized into 3 groups. Experimental animals received Compound I or nooglutyl intraperitoneously 30 minutes, 2, 24, and 48 hours after the surgery. Control animals at the same time points received saline (0.9% sodium chloride solution). 72 hours after OMCA the animals were decapitated. Material frozen at −20° C. was used for preparation of 5 frontal slices 2.5 mm thick, which were painted with 2,3,5-triphenyltetrazolium solution (TPTZ). Auc1 morphometric program was used to perform planimetria, determination of affected zone extent and percentage of affected zone extent in relation to volume of ipsilateral hemisphere. The surgery results in creation of vast ischemic damage of the brain cortex, which is localized within frontal-parietal and dorsal-lateral zones. To compare intensity of the changes in different slices arbitrary scale was used, with 75%, 60%, 45%, 20%, 5%, and 0% affection of hemisphere assessed as 2.5 points, 2 points, 1.5 points, 1 point, 0.5 points, and 0 points, respectively.

In control patients treated with saline total affected zone was 20.17±3.12%. Maximum ischemic damage was observed at the level of $2^{nd}$ and $3^{rd}$ slices (Table 3).

Compound I at 40 mg/kg used after ischemia-inducing exposure significantly reduced the extent of the damage at the level of three first slices (Table 3). Total affected area after the use of Compound I decreased to 10.54±1.84% (10.17±3.12% in the control group), and hence, the compound decreases total affected extent by 47.3% ($p<0.05$). Effect of nooglutyl was observed at higher dose level (50 mg/kg) and improvement was less pronounced (Table 3). Total affected area after nooglutyl administration reduced to 14.3±2.14%.

Thus, Compound I administered after ischemia-inducing exposure significantly attenuates intensity of morphological changes in cerebral cortex, which were caused by ligation of ipsilateral carotid. These results suggest neuroprotective effect of Compound I.

In separate series of the experiments the animals learned in the test of passive avoidance response (PAR), which was formed in apparatus supplied by Lafayette Instrument Co. (USA) comprising brightly illuminated hanging platform connected to dark chamber with electrified floor. In the course of learning the rat entered dark chamber due to congenital hole reflex, and received pain electric stimulus. Memory evaluation was carried out within 24 hours after learning session and comprised recording the number of animals, which did not enter dark chamber for 180 seconds, and latent period of entry for those animals, which came into the chamber.

Previously many control experiments with intact rats demonstrated that they usually did not enter dangerous chamber or enter the chamber at the very end of the test (average latent period is 145±10.1 seconds). In the control group of the animals with induced ischemia latent period of the entry to dark chamber decreased to 31.2±8.3 seconds (most animals did not remember the stimulus obtained the day before and quickly entered dangerous chamber). The animals with ischemia treated with nooglutyl or Compound I showed memory improvement manifested in greater latent period of entry to dark dangerous chamber: 56.2±8.3 seconds in nooglutyl-treated animals and 62.3±7.2 seconds in Compound I treated animals. These effects of nooglutyl and Compound Ia were significant compared with control at $p<0.05$.

EXAMPLE 7

Study of the Efficacy of Salt of N-Nicotinoyl Glutamic Acid (Compound I) and Nooglutyl in the Model of Intracerebral Posttraumatic Hematoma (Hemorrhagic Stroke)

White nondescript male rats with body weight 200-250 g, which lived in vivarium and had feed (standard palletized feed) and water ad libitum, with natural alternation of day and night, were used in the experiments. Hemorrhagic stroke (local cerebral hemorrhage) was simulated according to method by A. N. Makarenko et al. (Method of local hemorrhage simulation I various structures of the brain in experimental animals. Journal Visshei Nervnoy Deyatelnosti—Journal of Higher Nervous Activities, 2002, v. 52, No 6, p. 765-768). In nembutal-anesthetized rats (40 mg/kg, i.m.) destruction of the brain tissue in capsule interna area was made with the use of special device (mandarin-knife) followed by application of blood (0.02-0.03 ml) taken from under the rat's tongue to the damaged area (within 2-3 minutes). False-operated animals underwent scalping and craniotomy. The animals were divided into 5 groups: intact rats, false-operated rats, animals with hemorrhagic stroke received nooglutyl at 20 mg/kg, and animals with hemorrhagic stroke received Compound I at 20 mg/kg. Effects were recorded within 24 hours and 14 days after the surgery. Learning ability and memory of the rats was examined in the model of passive avoidance response (PAR, Passive Avoidance supplied by Lafayette Instrument Co., USA). To determine neurological deficit in the animals Stroke-index McGrow scale modified by I. V. Gannushkina (Functional architectonics of the brain, Moscow, Medicina, 1977, 224 p.) was used. The severity of the condition was determined by the sum of the points. The number of rats with mild symptoms up to 2.5 points of Stroke-index scale (apathy, weakness of the extremities, unilateral semiptosis, tremor, circus movements) and severe manifestations of neurological disorders (3 to 10 points)—paresis of the extremities, palsy of low extremities, lateral position. The animals received single dose of nooglutyl and Compound I at the same dose 20 mg/kg intraperitoneally within 3-3.5 hours after the surgery. Controlled animals were treated with saline. At onset of the experiment each group comprised 15-20 animals. Mortality of the rats was recorded throughout the observation period (14 days). Statistical analysis was made using parametrical and non-parametrical methods and Biostat software. Nimodipin administered at 01.mg/kg according to above scheme was considered as a standard.

Records of mortality showed that in the group of false-operated rats mortality was only 7% by Day 14, while in the group of animals with hemorrhagic stroke mortality reached 64%, and more than 56% of the animals died in first three days (Table 4). Nooglutyl exhibited strong protective potency. At the dose level 20 mg/kg this agent almost completely prevented the death of the animals throughout observation period: 20% (4 of 20) animals died. In the group treated with Compound I only 10% (2 of 20) animals died throughout observation period (14 days). Administration of Compound I in contrast to nooglutyl resulted in significant decrease in mortality already within the first day after the stroke. These results suggest high protective activity of Compound I in the animals experienced hemorrhagic stroke.

Examination of neurological status of survived animals using the scale Stroke-index McGrow showed that in the group of animals with hemorrhagic stroke on Day 1 of observation severe symptoms and signs were observed in 20% of the animals, while by Day 7 this category increased to 50% (Table 5). Nooglutyl and Compound I considerably reduced neurological deficit in animals. This effect was most pronounced on Day 14, when in control group of the animals with hemorrhagic stroke 60% of the rats had severe neurological symptoms. Administration of Nooglutil and Compound I resulted in reduction of this value to 25% and 15%, respectively. Thus, Compound I exhibited marked favourable effect on the course of neurological deficit development, and this effect was superior to that of nooglutyl.

The study of learning and memory processes in animals using PAR model showed that reproduction of the response 24 hours after learning by false-operated rats did not significantly differ from reproduction by intact animals and animals with hemorrhagic stroke either treated or non-treated with nooglutyl and Compound I (Table 6). 70-80% of the animas remembered electric shock in the dark chamber and did not enter it again. On reproduction of PAR on Day 14 other observations were made. 65% intact rats and 57% false-operated rats showed retention of memory trace, while only 8% of rats experienced hemorrhagic stroke remembered about electric shock. Treatment with nooglutyl at the dose level 20 mg/kg and Compound I at 20 mg/kg resulted in 5-fold increase and 6.5-fold of this value in the rats with HS, respectively, i.e. promoted longer retention of the memory trace (Table 6). Both agents significantly shortened latent period of entry into dark dangerous chamber. Nimodipin demonstrated weaker effect in this model.

Thus, the experiments demonstrated that pronounced neurological deficit, impaired learning and memory processes, and mortality of the animals with hemorrhagic stroke. This was associated with aggravation of abnormal symptoms by Day 14 of observation. The course of condition aggravation and mortality in the group of animals with HS may indicate failure of compensatory reactions of the organism enhancing on certain critical days (Day 3, Day 7, and Day 14) of postoperative period, and development of concomitant complications (edema, tissue swelling, disturbed intracerebral hemodynamics, high intracranial pressure, and cerebral ischemia).

Single administration of Compound I within 3-3.5 hours after creation of hemorrhagic stroke produced marked cerebroprotective effect preventing mortality of the rats and considerably attenuating neurological deficit, improving memory of the animals with posttraumatic hematoma-hemorrhagic stroke. In terms of cerebroprotective effect Compound I is superior to nooglutyl.

EXAMPLE 8

Study of the Efficacy of Salt of N-Nicotinoyl Glutamic Acid (Compound I) and Nooglutyl with Respect to Memory Disorders and Neurological Deficit in Aged Rats (24 Months)

White nondescript male rats (Wistar line): to adult animals at age 3 months with body weight 250-300 g and aged 24 month old animals with body weight 350-450 g were used in the study. Nooglutyl at dose level 20 mg/kg and Compound I were administered to aged rats intraperitoneally for 2 months followed by assessment of the effect on learning capacity impaired by age and neurological deficit. Analysis of variance with Student's test, variant portion method and U-test were employed for data processing.

Impact of Compound I on memory disorders in aged animals. To develop passive avoidance response (PAR) in rats the unit supplied by Lafayette Instrument Co., (USA) (Ader et al. Retention of a passive avoidance response as a function of the intensity and duration of electric shock. Psycho Sci. 1972, v. 26, p. 125-128; Voronina T. A. et al. "Textbook for Experimental (Preclinical Study) of novel pharmacological compounds". Moscow, Medicina. 2005, p. 253-263 and 308-320) was used. The unit was designed as small platform situated 1 m above the floor, which was illuminated with special lamp, and dark chamber with electrode floor The rat was placed on illuminated platform in front of the entry to the dark chamber with its tail directed to the entry, followed by recording of the latent period of response, the presence of the rat on illuminated platform, and the number of animals, which did not enter dark chamber. Animals preferring illuminated platform were not used in this experiment. In the dark chamber the animal received single pain stimulus with electric current (0.45 mA), duration of the stimulus was determined from the running out of the animal from the dark chamber. Test for PAR reproduction is to be carried out 24 hours after learning: the animals are repeatedly placed into the unit, and latent period of the first entry of the rat into dark experimental chamber and the number of the animals, which did not enter the chamber, are recorded.

The experiments showed that control 3 month old mice reproducing response 24 hours after learning session in 80% of cases did not enter dark chamber or entered with long latent period (table 7). Only 30% of the animals in the group of aged 24 month old rats reproduced learned response; remaining rats entered dark dangerous chamber with short latent period indicating memory impairment. Aged rats treated with Compound I reproduced response in 60% of cases. Nooglutyl also exhibited similar well-defined effect and improved reproduction of memory trace in 60% of rats. In addition, Compound I and nooglutyl significantly extended latent period of entry to the dark dangerous chamber.

To assess neurological deficit in aged animals (disturbed coordination and capacity for learning motor responses) the rats were placed on the rotating rod. The number of attempts required to obtain the skill of holding on the rotating rod for 2 minutes was registered. Experiment showed that 100% of young animals learned to hold on rotating (0.5 rpm) rod for 2 minutes after 5 placements (table 8). Under similar conditions only 25% of aged rats obtained this skill starting from the $11^{th}$-$14^{th}$ attempt. This suggests impairment of neurological status in aged rats and their reduced capacity for learning motor skills. 60% of aged rats treated with nooglutyl and 66% of aged rats treated with Compound I for 2 months learned the skill by the $10^{th}$ attempt. Analysis of the number of attempts required for learning to 50% of the animals showed that adult rats achieved this criterion by the first attempt, aged animals by the $17^{th}$ attempt, nooglutyl-treated aged animals by the $7^{th}$ attempt, and Compound Ia treated animals by the $6^{th}$ attempt.

Therefore, nooglutyl and Compound I exhibit pronounced geroprotective effect in the experiments with aged 24 month old rats, improving their memory and learning capacity and attenuating neurological deficit.

EXAMPLE 9

Study of Antidepressant Activity of Salt of N-Nicotinoyl Glutamic Acid (Compound I) in the Experiments with Mice SAM White nondescript mice and mice SAM P 10 (Takeda T. et al. Senescence-Accelerated Mouse (SAM): A novel murine model of accelerated senescence. J. Amer. Geriatr. Soc. 1991, v. 39, p. 911-919), with weight 26-31 g, exhibiting accelerated senescence at 11 months. The animals belonging to this line are characterized by genetically determined depression and impairment of learning capacity, which intensively aggravate starting from 6 months of age (accelerated senescence) (Miyamoto M., Characteristics of age-related behavioral changes in senescence-accelerated mouse SAMP8 and SAMP10. Exp. Gerontolol. 1997, v. 32, p. 139-148; Shimada A. et al. Age-related deterioration in conditional avoidance task in the SAM-P/10 mouse, an animal model of spontaneous brain atrophy. Brain Res., 1993, v. 608, p. 266-272). To assess depressive condition the method of forced swimming was used (Porsolt R. D. et al., Behavioral despair in rats: a new model sensitive to antidepressant treatment. Europ. J. Pharmacol., 1978, v. 47, p. 370-391). The mice were placed into cylinder 10 cm in diameter and 25 cm height. Cylinder was filled with water by ⅓ (27° C.). After unsuccessful attempts to get out of the water the animals have typical immovable posture, which is regarded as manifestation of "despair". Time of all active attempts of the animals to get out of the water within the first 6 minutes after submergence to water is recorded. Under the influence of antidepressants regardless of their mechanism the animals became more active and immobilization time reduces.

The experiments showed that mice SAM and considerably less active compared with nondescript animals, i.e. the period of active swimming of these animals is significantly shorter (Table 9). According to employed method this suggests more pronounced depression-like condition of mice SAM. All studied doses (5, 10, and 20 mg/kg) of Compound I extended time of active behavior of mice. This effect was most pronounced with the dose 20 mg/kg (P<0.03). Obtained results suggest antidepressant activity of Compound I. Effect of Compound I is comparable with that of amitryptilin.

EXAMPLE 10

Study of Anxiolytic Activity of Compound I in the Experiments on Mice SAM P10

White nondescript mice and mice SAM P 10 with weight 26-31 g, exhibiting accelerated senescence at 11 months. (Takeda T. et al. Senescence-Accelerated Mouse (SAM): A novel murine model of accelerated senescence. J. Amer. Geriatr. Soc. 1991, v. 39, p. 911-919). The animals belonging to this line are characterized by genetically determined depression and impairment of learning capacity, these symptoms intensively aggravate since 6 months of age (accelerated senescence) (Miyamoto M., Characteristics of age-related behavioral changes in senescence-accelerated mouse SAMP8 and SAMP10. Exp. Gerontolol. 1997, v. 32, p. 139-148; Shimada A. et al. Age-related deterioration in conditional avoidance task in the SAM-P/10 mouse, an animal model of spontaneous brain atrophy. Brain Res., 1993, v. 608, p. 266-272). Assessment of anxiety level of the mice was carried out under conditions of "elevated criss-cross labyrinth" (ECCL) method (Pellow S. et al. Validation of open: closed arm entries in elevated plus-maze as a measure of anxiety in the rat. Neurosci Meth J. 1985, No 14, p. 149-167; Voronina T. A. et al. "Textbook for Experimental (Preclinical Study) of novel pharmacological compounds". Moscow, Medicina. 2005, p. 253-263). Labyrinth comprises crossed bands 5×45 cm, with two opposed compartments having vertical walls 30 cm height (closed, dark arms), and two other compartments are open, light arms. Labyrinth is situated 30 cm above the floor. Central platform 50×50 cm is located at the cross of the planes. The mice were placed on the central platform with their tails directed to light arm. Time spent by the animals in open and closed arms, and the number of entering light and dark arms was registered. Total observation period comprised 5 minutes for each animal. Time spent in the open arms of the unit was considered as the measure of anxiolytic effect.

Experiment showed that control animals spent majority of 5 minute observation period in the closed arms of labyrinth. All studied doses (5, 10, and 20 mg/kg) of Compound I increased the main measure of animal's behavior—time spent in open, unprotected arms of labyrinth. Effect of the doses 10 and 20 mg/kg was statistically significant (Table 10). The highest effect was observed with Compound I at 20 mg/kg. Obtained results suggest that Compound I produced anxiolytic effect in the model of elevated criss-cross labyrinth.

EXAMPLE 11

Study of Acute Daily Toxicity of the Salt of N-Nicotinoyl Glutamic Acid (Compound I) in the Experiments on Mice The study of acute daily toxicity of Compound I was carried out on white nondescript male mice with body weight 25-28 g, which lived in habitual conditions in vivarium and received feed and water ad libitum. Single dose of Compound I was administered intraperitoneally. The animals were under observation for 2 days after the dosing. The dose levels of Compound I used in the toxicity study were as follows: 800 mg/kg, 1000 mg/kg, 1200 mg/kg, 1500 mg/kg, 1600 mg/kg. Compound I was dissolved in distilled water and administered in 0, 1 ml per 10 g of the body weight of the animal when the doses 800 mg/kg and 1000 mg/kg, and in 0.2 ml per 10 g of the body weight when the doses 1200 mg/kg, 1500 mg/kg, 1600 mg/kg were used. Control animals received distilled water in the volume 0.2 ml per 10 g of the body weight.

Each dose group comprised 10 animals. No mortality was observed in control animals, which received 0.2 ml of distilled water per 10 g of body weight. The results obtained in animals treated with Compound I are given in Table 11.

The experiments showed that Compound I at 1000 mg/kg, 1200 mg/kg, 1500 mg/kg, and 1600 mg/kg causes 20%, 60%, 90%, and 90% mortality in mice within 48 hours of observation. LD50 (the dose killing 50% of the animals) of Compound I comprises 1150 (1110÷1196) mg/kg. LD50 of nooglutyl is 1200 (1090÷1320) mg/kg. Thus, nooglutyl and Compound I have similar toxicity.

CONCLUSION

It was found that salts of N-oxynicotinoyl glutamic acid exhibit pronounced antiamnestic and antihypoxic activities. Compound I is the most effective with respect to effects, which are principal for nootrops and neuroprotectors. Antiamnestic and antihypoxic effects of Compound I is observed within the dose range from 5 to 120 mg/kg and is superior to nooglutyl.

Compound I showed distinct cerebroprotective effect in experimental models of ischemic and hemorrhagic strokes, preventing mortality of rats, attenuating neurological deficit and improving memory and learning processes. Cerebroprotective effects of Compound I are more pronounced and observed at lower doses compared with nooglutyl. Compound I is efficacious when administered to aged animals: it improves memory and motor functions.

The presence of antidepressant and anxiolytic effects in pharmacological spectrum of Compound I is important advantage of Compound I over nooglutyl. These effects can be revealed in the model of depression-like condition in the forced swimming test and in the model of anxiety in the test with elevated criss-cross labyrinth. Compound I also produces neuroprotective effect, which is manifested by its ability to restore brain areas damaged by the stroke, and heroprotective effect, which is characterized by improvement of neurological deficits, cognitive functions and physical performance.

TABLE 1

Antihypoxic effects of the salts of N-nicotinoyl glutamic acids (Compounds I-III) and nooglutyl

| Compound | Dose, mg/kg | Life interval of mice (minutes) exposed to hypobaric hypoxia | Life interval of mice (minutes) exposed to hypoxia in hermovolume |
|---|---|---|---|
| Control | Distilled water | 3.63 ± 0.31 | 14.3 ± 0.51 |
| Nooglutyl | 30 | 4.1 ± 0.77 | 13.9 ± 0.42 |
|  | 60 | 7.68 ± 0.54* | 15.2 ± 0.39 |
|  | 120 |  | 16.4 ± 0.53* |
| Compound I | 30 | 6.51 ± 0.82* | 16.2 ± 0.31* |
|  | 60 | 9.17 ± 0.91* | 17.8 ± 0.41* |
|  | 120 |  | 18.1 ± 0.48* |
| Compound II | 30 | 6.51 ± 0.82* | 14.1 ± 0.71 |
|  | 60 | 5.95 ± 0.84* | 16.3 ± 0.64 |
|  | 120 |  | 17.8 ± 0.69* |
| Compound III | 30 | 3.91 ± 0.63 | 14.2 ± 0.39 |
|  | 60 | 5.52 ± 0.54* | 15.9 ± 0.45 |
|  | 120 |  | 17.4 ± 0.65* |

*Significant difference between control and experimental group, $P < 0.05$ (Mann-Whitney U-test).

TABLE 2

Antiamnestic effects of the salts of N-nicotinoyl glutamic acids (Compounds I-III) and nooglutyl

| Compound | Dose, mg/kg | Time of presence of animals while PAR reproduction (seconds) on the illuminated platform | in the dark chamber |
|---|---|---|---|
| Control without amnesia | Distilled water | 98.2 ± 18.4 | 21.8 ± 5.2 |
| Control with amnesia | Distilled water | 32.3 ± 7.2* | 87.7 ± 12.3* |
| Nooglutyl | 25 | 46.7 ± 13.4 | 73.3 ± 13.4 |
|  | 50 | 54.3 ± 10.2** | 65.7 ± 7.1** |
| Compound I | 25 | 55.8 ± 9.3** | 64.2 ± 6.4** |
|  | 50 | 79.4 ± 12.8** | 40.6 ± 8.3** |
| Compound II | 25 | 41.3 ± 11.6 | 78.7 ± 12.3 |
|  | 50 | 52.5 ± 12.3** | 67.5 ± 15.1** |
| Compound III | 25 | 49.3 ± 10.1 | 70.7 ± 9.4 |
|  | 50 | 51.4 ± 9.8** | 68.6 ± 7.1** |

*Significant difference between control with amnesia and control without amnesia, $P < 0.05$;
**Significant difference between control with amnesia and effect of study compounds, $P < 0.05$ (Mann-Whitney U-test).

TABLE 3

Effects of the salt of N-nicotinoyl glutamic acid (Compound I) and nooglutyl in the model of massive cortical ischemia on intensity of ischemic damage of cerebral cortex (slice score, points)

| Compound | Slice 1 | 2 | 3 | 4 | 5 |
|---|---|---|---|---|---|
| Saline (n = 10) | 0.6 ± 0.1 | 1.52 ± 0.15 | 1.45 ± 0.18 | 0.74 ± 0.21 | 0.23 ± 0.17 |
| Nooglutyl, 50 mg/kg (n = 9) | 0.28 ± 0.06* | 1.12 ± 0.17* | 1.01 ± 0.11* | 0.59 ± 0.19 | 0.18 ± 0.14 |
| Compound I, 40 mg/kg (n = 10) | 0.08 ± 0.01* | 0.92 ± 0.12* | 0.7 ± 0.19* | 0.58 ± 0.14 | 0.2 ± 0.15 |

*$p < 0.05$ (Student's test)

TABLE 4

Effect of the salt of N-nicotinoyl glutamic acid (Compound I) and nooglutyl on survival of the animal experienced hemorrhagic stroke

| Groups of animals | Doses, mg/kg | Day 1 after surgery absolute | % | Day 3 after surgery absolute | % | Day 7 after surgery absolute | % | Day 14 after surgery absolute | % |
|---|---|---|---|---|---|---|---|---|---|
| | | Number of animals, which died within 14 days after hemorrhagic stroke in relation to total number of operated animals (absolute value and percentage) | | | | | | | |
| False-operated | | 0 of 14 | 0 | 0 of 14 | 0 | 0 of 14 | 0 | 1 of 14 | 7 |
| Stroke | | 12 of 36 | 30* | 20 of 36 | 56* | 20 of 36 | 56* | 23 of 36 | 64* |
| Stroke + nooglutyl | 20 | 3 of 20 | 15 | 4 of 20 | 20# | 4 of 20 | 20# | 4 of 20 | 20## |
| Stroke + compound I | 20 | 1 of 20 | 5 | 2 of 20 | 10## | 2 of 20 | 10## | 2 of 20 | 10## |

Significant difference between the group of false-operated animals and group of animals with hemorrhagic stroke,
*$P \leq 0.001$ ($\chi 2$); between the control group of animals with hemorrhagic stroke and the groups of treated animals with HS,
$P \leq 0.01$ ($\chi 2$);
$P \leq 0.001$ ($\chi 2$).

TABLE 5

Effect of the salt of N-nicotinoyl glutamic acid (Compound I) and nooglutyl on neurological deficit in rats after hemorrhagic stroke (McGrow Scale)

| Neurological symptoms | Number of animals with neurological symptoms, % | | | | | |
|---|---|---|---|---|---|---|
| | Stroke (control) | | Stroke + Nooglutyl | | Stroke + Compound I | |
| | Day 1 | Day 14 | Day 1 | Day 14 | Day 1 | Day 14 |
| Weakness of extremities | 60 | 20 | 30* | 10 | 20* | 0 |
| Circus movements | 10 | 10 | 5 | 0 | 10 | 10 |
| Paresis of 1-4 extremities | 10 | 50 | 25 | 20* | 10 | 5* |
| Palsy of 1-4 extremities | 20 | 20 | 0 | 0 | 0 | 0 |

*Significant difference between the rats with hemorrhagic stroke (control) and treated animals, $P \leq 0.001$ ($\chi 2$).

TABLE 6

Effect of the salt of N-nicotinoyl glutamic acid (Compound I) and nooglutyl on reproduction of passive avoidance response by rats with hemorrhagic stroke 24 hours and 14 days after learning

| Groups of rats | PAR reproduction within: | | | |
|---|---|---|---|---|
| | 24 hours | | 14 days | |
| | Latent period of entry to dark chamber (c) | Number of animals, which did not enter dark chamber (%) | Latent period of entry to dark chamber (c) | Number of animals, which did not enter dark chamber (%) |
| Intact | 174.2 ± 24.5 | 80 | 124.3 ± 26.5 | 65 |
| False-operated | 10.3 ± 18.4 | 70 | 105.1 ± 21.7 | 57 |
| Stroke | 126.7 ± 17.5 | 60 | 29.6 ± 7.6** | 8* |
| Stroke + Nooglutyl, 20 mg/kg | 130.4 ± 20.1 | 64 | 92.2 ± 18.2# | 40$ |
| Stroke + Compound I, 20 mg/kg | 128.1 ± 17.6 | 63 | 98.9 ± 21.3# | 52$$ |

TABLE 6-continued

Effect of the salt of N-nicotinoyl glutamic acid (Compound I) and nooglutyl on reproduction of passive avoidance response by rats with hemorrhagic stroke 24 hours and 14 days after learning

| Groups of rats | PAR reproduction within: | | | |
|---|---|---|---|---|
| | 24 hours | | 14 days | |
| | Latent period of entry to dark chamber (c) | Number of animals, which did not enter dark chamber (%) | Latent period of entry to dark chamber (c) | Number of animals, which did not enter dark chamber (%) |
| Stroke + Nimodipin | 123.7 ± 19.6 | 58 | 77.5 ± 32.8 | 33$ |

Significant difference between the group of false-operated animals and animals with hemorrhagic stroke:
**$P \leq 0.01$ (Mann-Whitney U-test),
*$P \leq 0.001$ ($\chi 2$);
significant difference between the group of animals with hemorrhagic stroke and treated animals with HS:
$$P \leq 0.05$;
$$$P \leq 0.001$ ($\chi 2$).

TABLE 7

Effect of the salt of N-nicotinoyl glutamic acid (Compound I) and nooglutyl on reproduction of passive avoidance response by aged rats (24 months)

| Compound | Age (months) | Dose/ (administration period) | PAR reproduction 24 hours after learning | |
|---|---|---|---|---|
| | | | Latent period of entry to dark chamber (c) | Number of the rats, which did not entry dark chamber (%) |
| Control | 3 | Distilled water/ 60 days | 169.3 ± 25.5 | 80 |
| Control | 24 | Distilled water/ 60 days | 64.2 ± 14.8* | 30^ |
| Nooglutyl | 24 | 20 mg/kg 60 days | 97.1 ± 20.3 | 60# |
| Compound I | 24 | 20 mg/kg 60 days | 96.9 ± 16.1 | 60# |

*Significant difference between the groups of young and aged rats $P \leq 0.05$ (Mann-Whitney U-test),
^$P \leq 0.05$ ($\chi 2$);
Significant difference between the group of control rats and group of treated animals, $P \leq 0.05$ ($\chi 2$).

TABLE 8

Effect of the salt of N-nicotinoyl glutamic acid (Compound I) and nooglutyl on motor coordination of aged (24 months) rats in the experiment with rotating rod

| Compound | Age (months) | Dose/ Administration period | Number of the animals (%), which obtained the skill | | |
|---|---|---|---|---|---|
| | | | By attempt 5 | By attempt 10 | By attempt 15 |
| Control | 3 | Distilled water/ 60 days | 100 | 100 | 100 |
| Control | 24 | Distilled water/ 60 days | 0 | 20* | 25* |
| Nooglutyl | 24 | 20 mg/kg 60 days | 20 | 60# | 60# |
| Compound I | 24 | 20 mg/kg 60 days | 20 | 60# | 66# |

*Significant difference between the groups of young and aged animals, $P \leq 0.05$.
Significant difference between the groups of control aged rats and treated aged rats, $P \leq 0.05$ ($\chi 2$).

TABLE 9

Study of antidepressant activity of Compound I in the experiments on mice SAM

| Compound | Mice species | Dose, mg/kg | Period of active behaviour, seconds |
|---|---|---|---|
| Control | nondescript | Distilled water | 260.2 ± 24.8 |
| Control | SAM | Distilled water | 147.00 ± 5.96* |
| Compound I | SAM | 5 | 1760.10 ±± 9.58 |
| Compound I | SAM | 10 | 190.00 ± 9.50# |
| Compound I | SAM | 20 | 225.00 ± 10.97# |
| Control | SAM | Distilled water | 142.50 ± 25.42 |
| Amitryptilin | SAM | 10 | 225.10 ± 25.19# |

*Significant difference between nondescript mice and SAM mice, $P \leq 0.05$ (Student's test);
Significant difference between control SAM group and treated SAM group, $P \leq 0.05$ (Student's test).

TABLE 10

Study of anxiolytic activity of Compound I in the experiments on mice SAM P 10 under conditions of elevated criss-cross labyrinth

| Groups of animals | Dose, mg/kg | Time spent in the closed arms (c) | Number of entries the closed arms | Time spent in the opened arms (c) | Number of entries the opened arms |
|---|---|---|---|---|---|
| Control | Distilled water | 264.9 ± 8.0 | 15.3 ± 1.8 | 12.0 ± 3.3 | 6.2 ± 0.9 |
| Compound I | 5 | 247.0 ± 6.4 | 15.6 ± 2.1 | 21.1 ± 4.6 | 5.7 ± 0.6 |
|  | 10 | 262.0 ± 22.1 | 20.51 ± 3.1 | 23.9 ± 5.8* | 7.7 ± 0.2 |
|  | 20 | 234.8 ± 8.7* | 19.3 ± 2.5 | 28.4 ± 6.2 | 13.0 ± 1.1* |

*Significant difference between control group of mice and group of treated mice, $P \leq 0.05$ (Student's test)

TABLE 11

Acute toxicity of Compound I

| Doses, mg/kg | Died animals, % | Factors | LD50 | LD16 | LD84 |
|---|---|---|---|---|---|
| 800 | 0 | S-1.1 | 1150 | 900 | 1450 |
| 1000 | 20 | N-50 | (1110 ± 1196) | | |
| 1200 | 60 | f-1.04 | | | |
| 1500 | 90 | | | | |
| 1600 | 100 | | | | |

The invention claimed is:

1. A mono- or divalent salt of N-(5-hydroxynicotinoyl)-L-glutamic acid of the formula

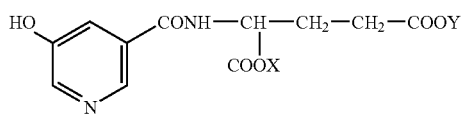

wherein

X=CaOH, Y=H (I), or

X=Y=Na (II), or

X=Y=K (III), which exhibit antidepressant, anxiolytic, neuroprotective, cerebroprotective, heroprotective, nootropic, antihypoxic activities and also psychotropic and neuroprotective effects.

* * * * *